(12) United States Patent
Huh

(10) Patent No.: US 12,161,590 B2
(45) Date of Patent: Dec. 10, 2024

(54) WELDING PROTECTOR COMPRISING PANEL AND AR COATING LAYER

(71) Applicant: OTOS WING CO., LTD., Seoul (KR)

(72) Inventor: Sung Won Huh, Seoul (KR)

(73) Assignee: OTOS WING CO., LTD., Seoul (KR)

( * ) Notice: Subject to any disclaimer, the term of this patent is extended or adjusted under 35 U.S.C. 154(b) by 388 days.

(21) Appl. No.: 17/414,281

(22) PCT Filed: Sep. 18, 2020

(86) PCT No.: PCT/KR2020/012600
§ 371 (c)(1),
(2) Date: Jun. 15, 2021

(87) PCT Pub. No.: WO2021/054754
PCT Pub. Date: Mar. 25, 2021

(65) Prior Publication Data
US 2022/0062051 A1    Mar. 3, 2022

(30) Foreign Application Priority Data

Sep. 20, 2019   (KR) .......................... 10-2019-0116360

(51) Int. Cl.
*A61F 9/06* (2006.01)
*F16P 1/06* (2006.01)

(52) U.S. Cl.
CPC .............. *A61F 9/062* (2013.01); *A61F 9/061* (2013.01); *F16P 1/06* (2013.01)

(58) Field of Classification Search
CPC .. A61F 9/062; A61F 9/061; A61F 9/06; A61F 9/04; A61F 9/064; A61F 9/067; A42B 1/08; A42B 3/22; A42B 3/225; A42B 3/222; A42B 3/223; A42B 3/221;
(Continued)

(56) References Cited

U.S. PATENT DOCUMENTS 2,445,355 A * 7/1948 Hurt .......................... G02C 3/02
                                                                2/10
5,739,797 A * 4/1998 Karasawa .......... G02B 27/0172
                                                              359/632
(Continued)

FOREIGN PATENT DOCUMENTS

KR    10-2004-0082771 A    9/2004
KR         10-0658036 B1    12/2006
(Continued)

OTHER PUBLICATIONS

International Search Report and Written Opinion mailed Mar. 22, 2021 in related foreign application No. PCT/US2020/012600, all pgs.

*Primary Examiner* — Khoa D Huynh
*Assistant Examiner* — Uyen T Nguyen
(74) *Attorney, Agent, or Firm* — Kilpatrick Townsend & Stockton LLP

(57) ABSTRACT

Embodiments of the present disclosure provide a welding protector including a helmet unit, a mounting frame unit, a cartridge unit including an information display portion, and a movement control unit, and allowing an operator to directly view related work information through the information display portion during welding operation to improve user convenience.

3 Claims, 19 Drawing Sheets

(58) Field of Classification Search
CPC ......... A42B 3/224; A42B 3/226; A42B 3/227; A42B 3/228; A42B 3/26
USPC ............................................................ 2/8.3
See application file for complete search history.

(56) References Cited

U.S. PATENT DOCUMENTS

| | | | |
|---|---|---|---|
| 6,457,180 B1* | 10/2002 | Jung | A42B 1/0184 |
| | | | 2/424 |
| 8,063,934 B2* | 11/2011 | Donato | G08B 13/19621 |
| | | | 348/82 |
| 9,696,552 B1* | 7/2017 | Goergen | A42B 1/24 |
| 10,154,704 B1* | 12/2018 | Caito, III | A42B 3/223 |
| 2002/0135872 A1* | 9/2002 | Choinere | G02B 23/125 |
| | | | 359/409 |
| 2010/0287676 A1* | 11/2010 | Seo | A61F 9/064 |
| | | | 2/8.2 |
| 2016/0125653 A1* | 5/2016 | Denis | G06F 3/012 |
| | | | 348/90 |
| 2016/0227866 A1* | 8/2016 | Tal | F41G 3/225 |
| 2018/0148578 A1* | 5/2018 | Ohta | C08J 3/28 |

FOREIGN PATENT DOCUMENTS

| | | |
|---|---|---|
| KR | 10-0814366 B1 | 3/2008 |
| KR | 10-2012-0091543 A | 8/2012 |
| KR | 10-2012-0097653 A | 9/2012 |

\* cited by examiner

WELDING PROTECTOR COMPRISING PANEL AND AR COATING LAYER

TECHNICAL FIELD

Embodiments of the present disclosure relate to a welding protector including a PANEL and an anti-reflection coating layer, and in more detail, a welding protector that may improve user convenience since an operator may directly view related work information during a welding operation.

BACKGROUND ART

Welding is to join two metals by locally heating and melting a metal using the fusibility of the metal. In such a welding operation, high heat and high brightness light and gas are generated, so the operator wears a welding protector as one of a protective equipment.

The welding protector is used to protect an operator's face and eyes during welding or cutting. In addition, an anti-glare device (hereinafter referred to as a cartridge) for protecting the operator's eyes from intense harmful light generated during work such as welding or cutting is mounted on the welding protector.

Such a cartridge typically blocks light having a wavelength that is greater than or equal to 780 nm and less than 365 nm, and controls the amount of visible light to be transmitted, so that a welding position may be visually checked without glare.

In the conventional cartridge, information related to the welding operation is not in the field of view of the operator during the welding operation, so that the operator has to take off the welding protector to check the information related to the welding operation.

DESCRIPTION OF EMBODIMENTS

Technical Problem

The present disclosure is to solve the above problems and provides a welding protector improving user convenience by including an information display portion provided in a cartridge unit to allow an operator to directly check related information during a welding operation.

In addition, the present disclosure provides a welding protector capable of easily adjusting the distance between the operator's eyes and the information display portion through hinge coupling.

However, these problems are exemplary, and the scope of the present disclosure is not limited thereto.

Solution to Problem

Embodiments of the present disclosure provide a welding protector for protecting an operator including a helmet unit having an opening and a shield portion surrounding the opening; a mounting frame unit attachable to and detachable from the shield portion; and a cartridge unit coupled to the mounting frame unit and disposed on a path of light generated during a welding operation, wherein the cartridge unit includes a filter portion; a panel portion coupled to the filter portion and disposed relatively closer to a face side of the operator than the filter portion; a glass portion disposed relatively closer to the face side of the operator than the panel portion; and an information display portion combined with the glass portion and visually displaying work information.

In the present disclosure, the information display portion may contact and be coupled to the front or rear surface of the glass portion.

In the present disclosure, the information display portion may include LCD panel made of a transparent material.

In the present disclosure, the information display portion may further include an irradiation unit formed of an anti-reflection (AR) coating layer made of a transparent material, installed inside the helmet unit and irradiating a light source to the information display portion.

In the present disclosure, the light source irradiated from the irradiation unit may be irradiated at a predetermined angle with one surface of the information display portion.

In the present disclosure, one end of the mounting frame unit may be hinged to the shield portion.

In the present disclosure, one end of the cartridge unit may be hinged to the mounting frame unit.

Other aspects, features, and advantages other than those described above will become apparent from the following drawings, claims, and detailed description of the disclosure.

Advantageous Effects of Disclosure

In the welding protector according to the present disclosure, work information display portion formed of a transparent material is disposed on the front or rear side of a glass portion, and information related to the welding operation is visually displayed, so that the operator may check directly and immediately work information related to welding operation without taking off a helmet unit, thus user convenience is improved.

In addition, since the mounting frame unit is hinged to the helmet unit, there is an effect that an opening may be opened and closed according to the convenience of the operator.

In addition, since a cartridge unit is hinged to the mounting frame unit, there is an effect that the distance from the operator's eyes for securing a view of the information display portion may be adjusted.

In addition, since the information display portion includes an anti-reflection coating layer made of a transparent material, a refractive index of visible light is lowered to improve transmittance, the diffuse reflection of visible light passing through the panel portion may be minimized, and clear vision may be secured during welding operation.

BEST MODE

Figure 1:
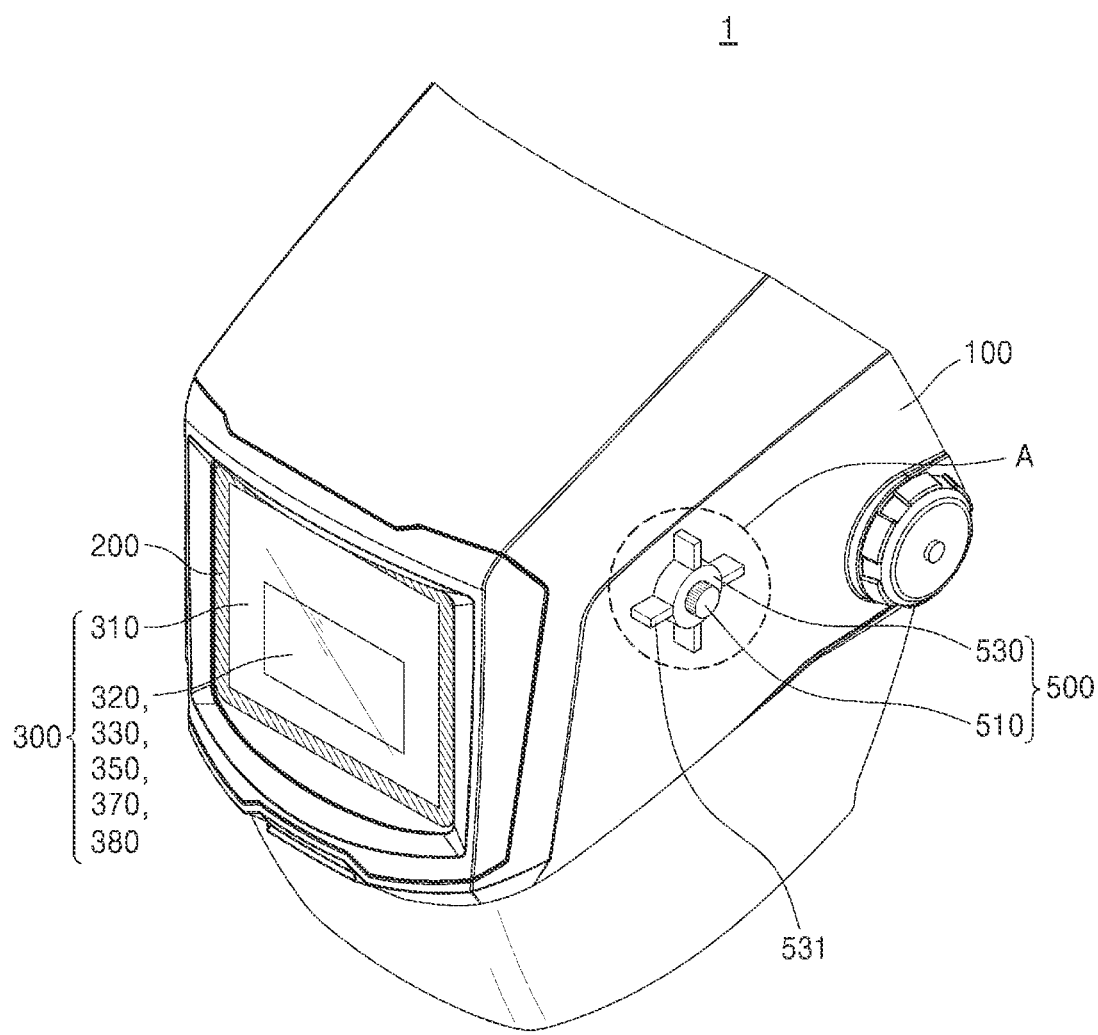
FIG. 1 is a perspective view illustrating a welding protector according to an embodiment of the present disclosure.

Embodiments of the present disclosure provide a welding protector for protecting an operator including a helmet unit having an opening and a shield portion surrounding the opening; a mounting frame unit attachable to and detachable from the shield portion; and a cartridge unit coupled to the mounting frame unit and disposed on a path of light generated during a welding operation, wherein the cartridge unit includes a filter portion; a panel portion coupled to the filter portion and disposed on a face side of the operator relative to the filter portion; a glass portion disposed relatively closer to the face side of the operator than the panel portion; and an information display portion combined with the glass portion and visually displaying work information.

MODE OF DISCLOSURE

Since the present disclosure may apply various transforms and have various embodiments, specific embodiments will be illustrated in the drawings and described in detail in the detailed description. The effects and features of the present disclosure and methods of achieving the same will become clear with reference to the embodiments described in detail below together with the drawings. However, the present disclosure is not limited to the embodiments disclosed below, but may be implemented in various forms.

Hereinafter, embodiments of the present disclosure will be described in detail with reference to the accompanying drawings, and the same or corresponding elements will be designated by the same reference numerals when described with reference to the accompanying drawings, and redundant descriptions thereof will be omitted.

In the following embodiments, the terms "first", "second", etc. are not limited but are used to distinguish one component from another.

In the following embodiments, a singular expression includes a plurality of expressions unless clearly indicated in the context otherwise.

In the following embodiments, the term "including" or "having" means that a feature, or component, described in the specification, is present, and does not preclude the possibility of adding one or more other features or component.

In the following embodiments, when a portion of a film, a region, a component, and the like is disposed on or on another portion, the portion may be disposed directly on the other portion, and also another film, a region, a component, and the like may be interposed therebetween.

In the drawings, the sizes of the elements may be exaggerated or reduced for convenience of description. For example, the size and thickness of each component shown in the drawings are arbitrarily shown for convenience of description, and thus the present disclosure is not necessarily limited to the illustration.

If any embodiment is implementable otherwise, the particular process order may be performed differently from the order described. For example, two processes that are continuously described may be performed substantially simultaneously, or may be performed in an order opposite to the order described.

In the following embodiments, when "a film", "a region", and "a component" are connected, "the film", "the region", and "the component" may be directly connected to another film, region, and component, or may be connected with another film, region, and component with an intervening film, region, and component therebetween. For example, in the present specification, when a film, a region, a component, and the like are electrically connected, included are not only the case in which the film, the region, the component, and the like are directly electrically connected to another film, region, and component, but also the case in which the film, the region, the component, and the like are indirectly electrically connected to another film, region, and component, with intervening film, region, and component therebetween.

Figure 2A:
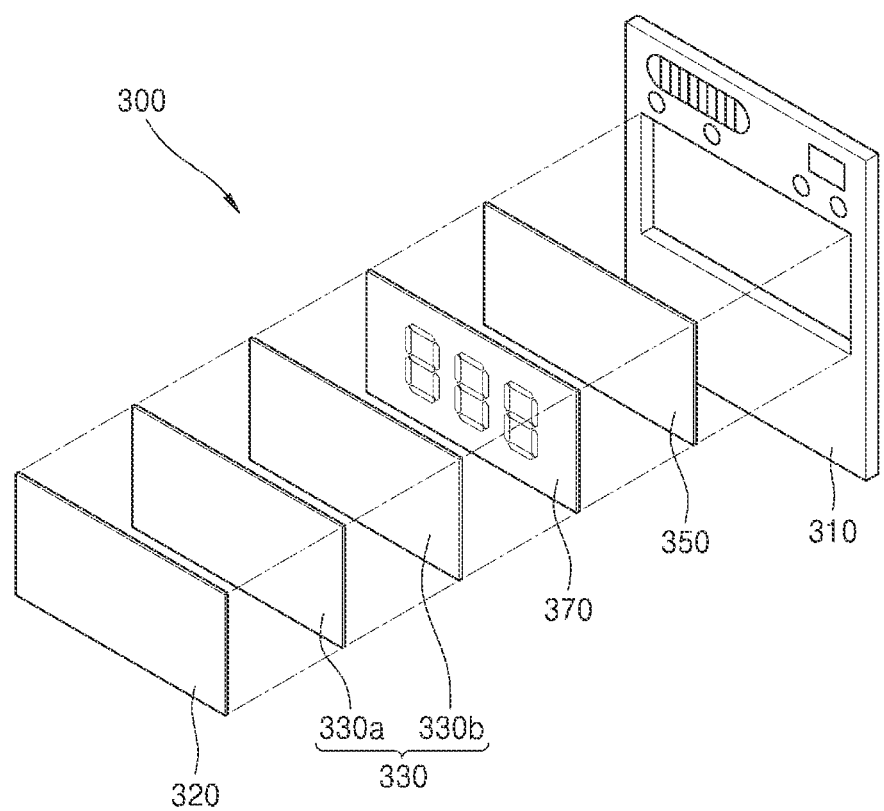
FIG. 2A is an exploded perspective view illustrating a cartridge unit according to an embodiment of the present disclosure.
Figure 4:
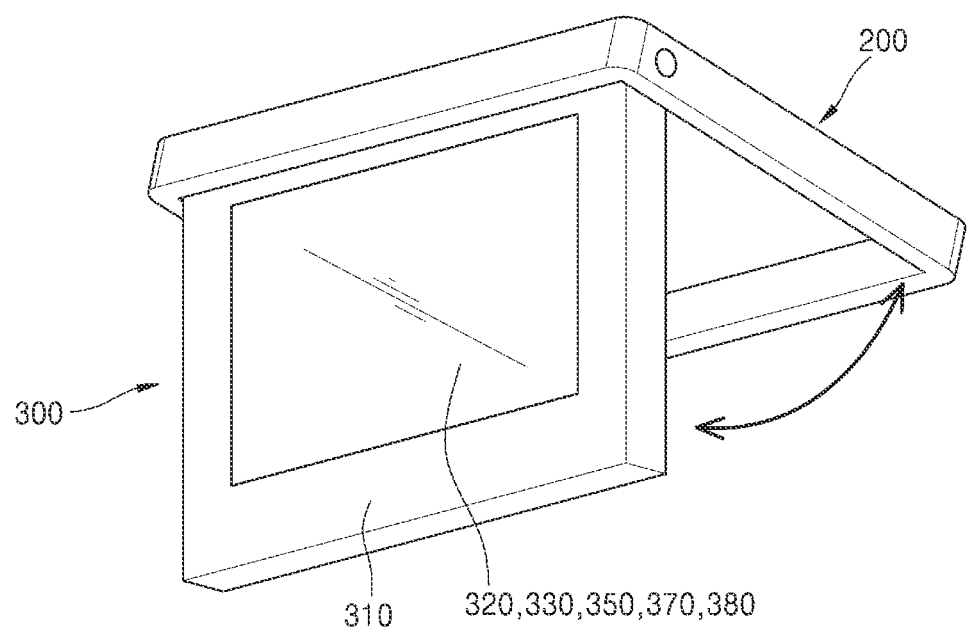
FIG. 4 is a diagram illustrating a state in which a mounting frame unit and the cartridge unit are combined with each other according to an embodiment of the present disclosure.
Figure 5A:
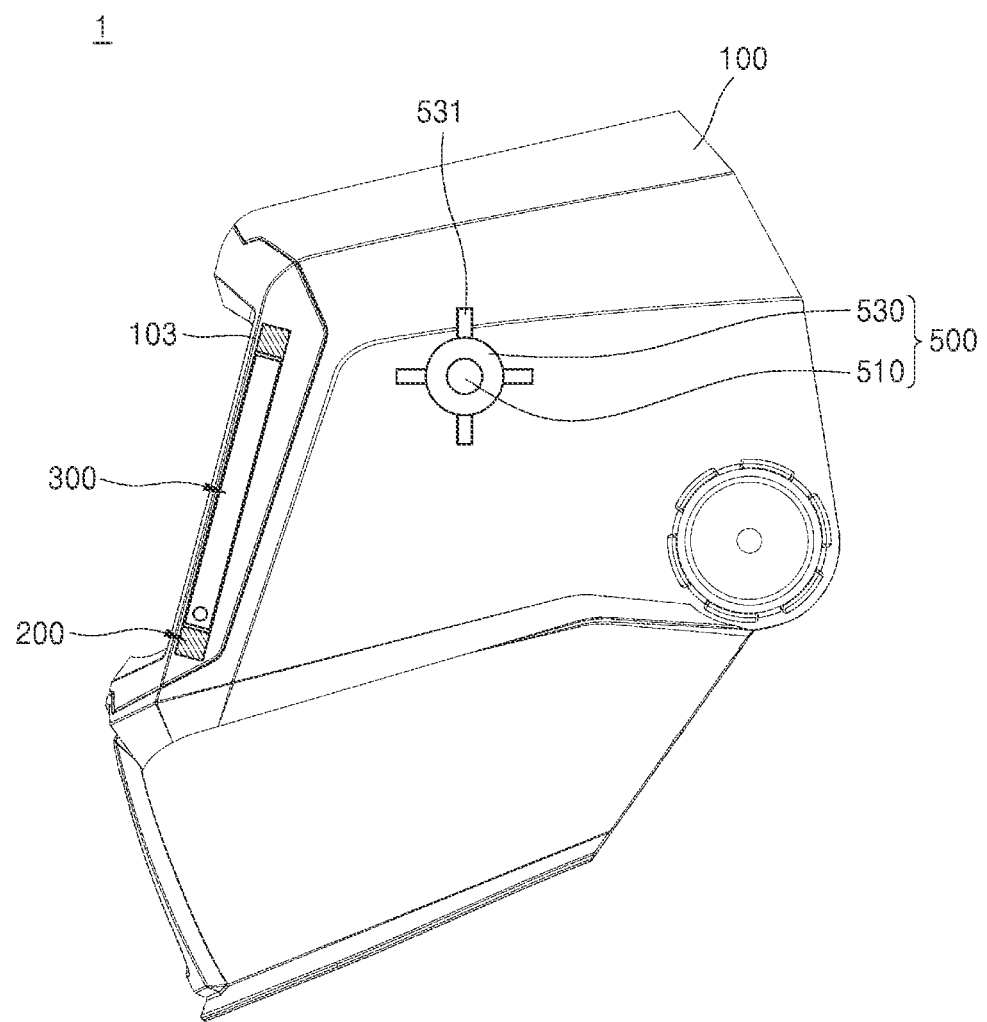
FIGS. 5A to 5C are diagrams illustrating an unfolded state of the mounting frame unit and the cartridge unit according to an embodiment of the present disclosure.
Figure 5B:
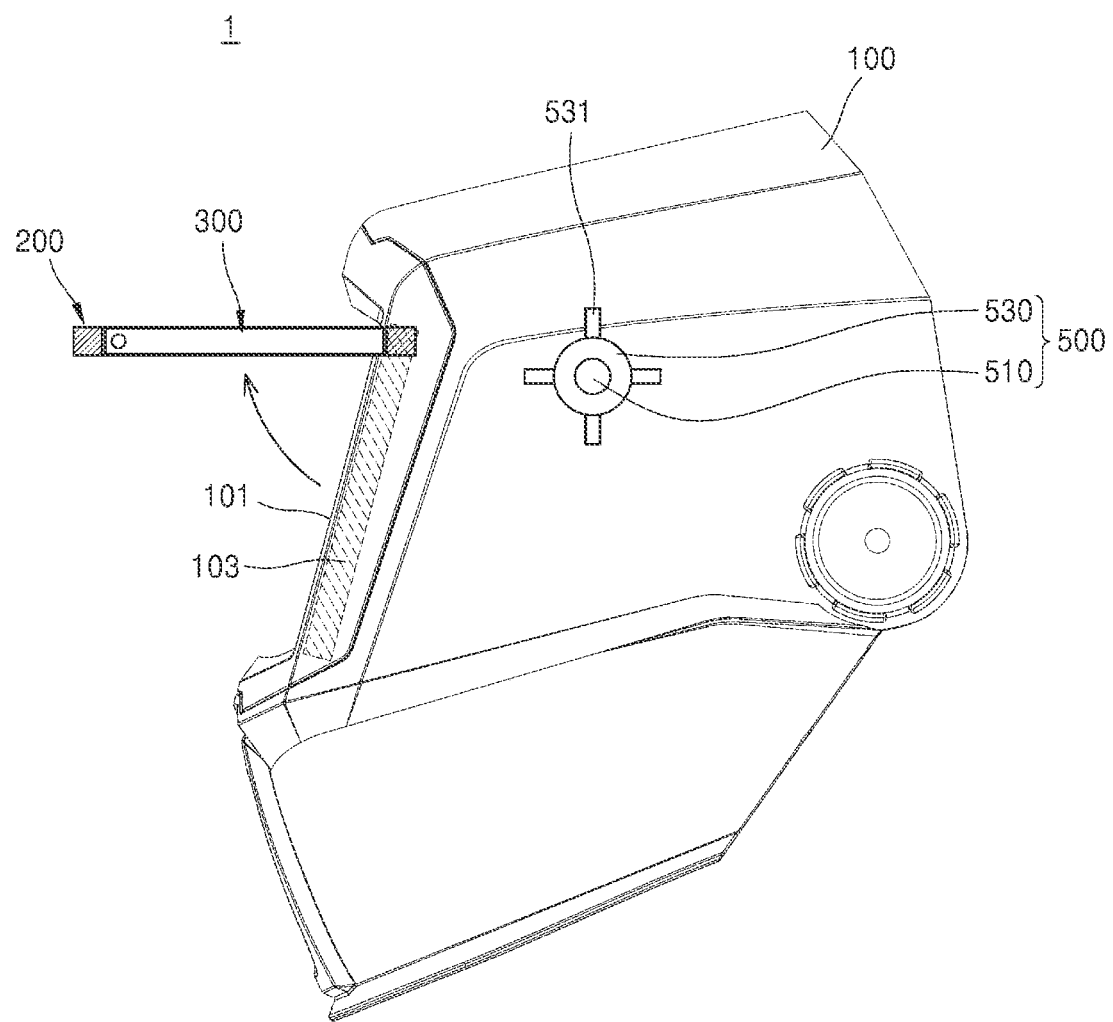
Figure 5C:
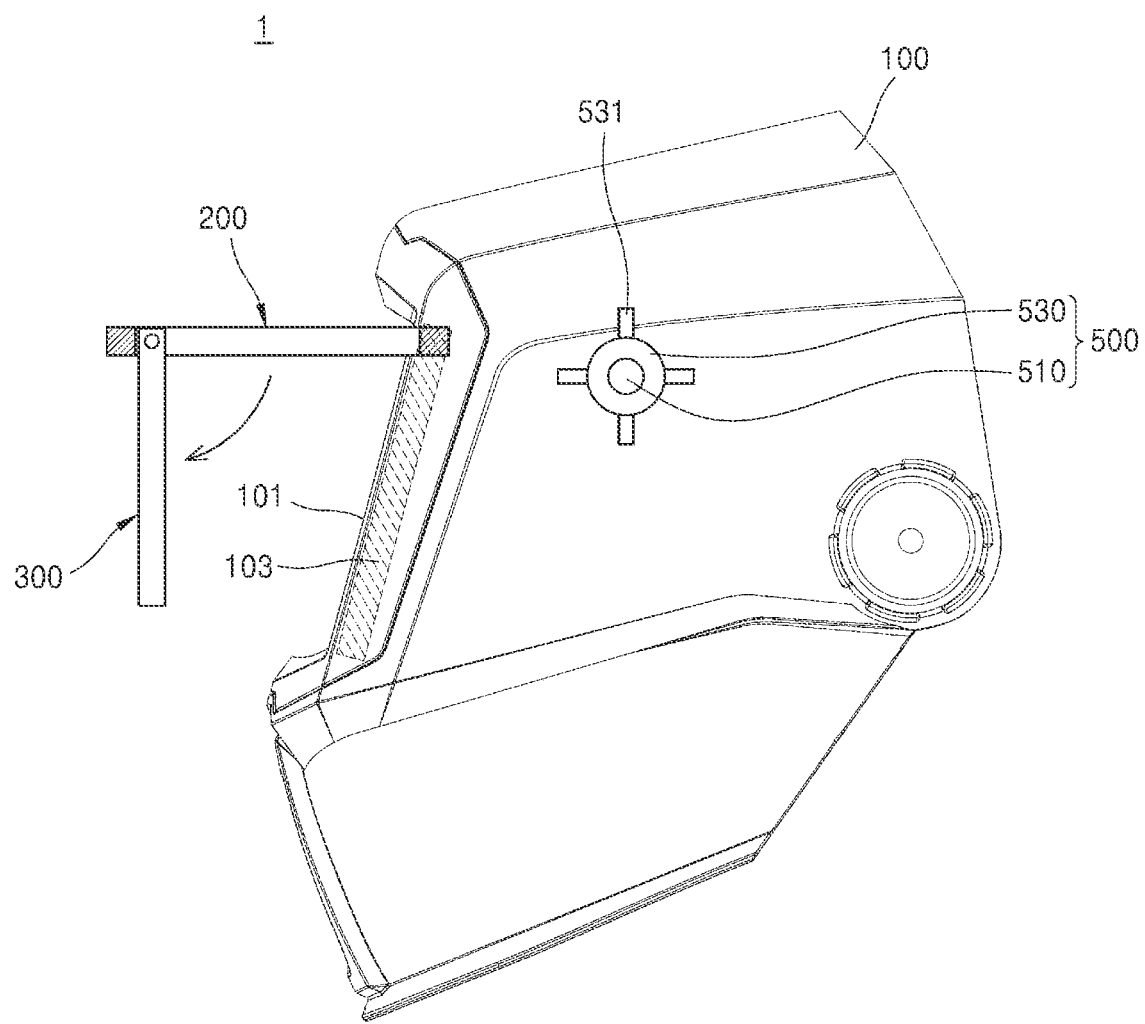
Figure 6:
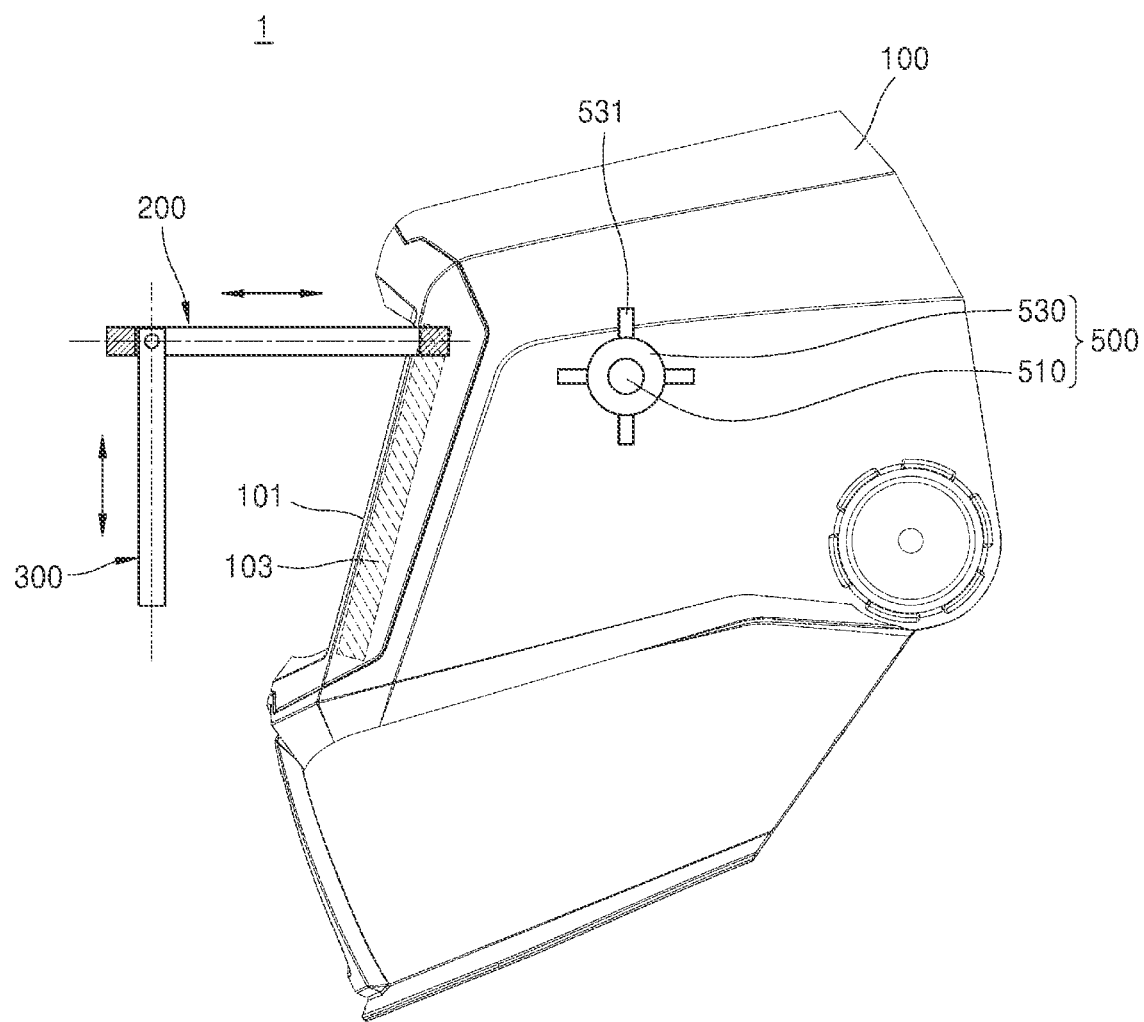
FIG. 6 is a side view illustrating the welding protector according to an embodiment of the present disclosure.
Figure 7:
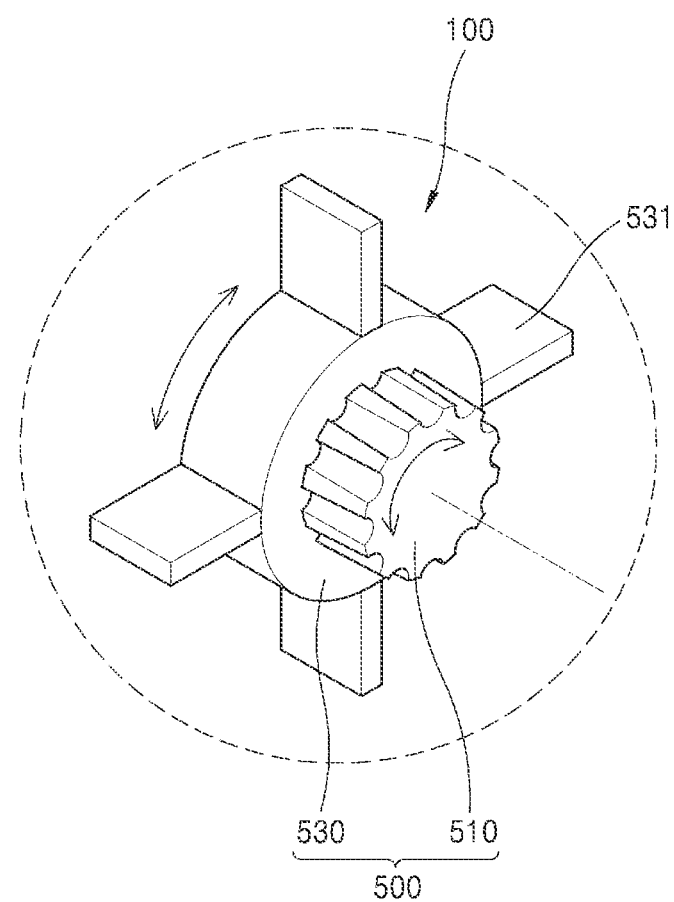
FIG. 7 is an enlarged view of part A of FIG. 1.

FIG. 1 is a perspective view illustrating a welding protector according to an embodiment of the present disclosure. FIG. 2A is an exploded perspective view illustrating a cartridge unit according to an embodiment of the present disclosure. FIGS. 3A to 3J are rear views illustrating the cartridge unit according to embodiments of the present disclosure. FIG. 4 is a diagram illustrating a state in which a mounting frame unit and the cartridge unit are combined with each other according to an embodiment of the present disclosure. FIGS. 5A to 5C are diagrams illustrating an unfolded state of the mounting frame unit and the cartridge unit according to an embodiment of the present disclosure. FIG. 6 is a side view illustrating the welding protector according to an embodiment of the present disclosure. FIG. 7 is an enlarged view of part A of FIG. 1.

Referring to FIGS. 1, 2A and 4 to 7, a welding protector 1 according to an embodiment of the present disclosure is for protecting an operator during a welding operation, and may include a helmet unit 100, a mounting frame unit 200, a cartridge unit 300 and a movement control unit 500.

Referring to FIGS. 1, 2A and 4 to 7, the helmet unit 100 according to an embodiment of the present disclosure forms an exterior of the welding protector 1, and may block fire generated during a welding operation from reaching the operator's face, thereby preventing safety accidents that may occur to the operator.

An opening 101 may be formed on the front surface of the helmet unit 100 (based on FIG. 1), and a shield portion 103 may be provided to surround the opening 101. The mounting frame unit 200 to be described later may be disposed to be attachable to and detachable from the shield portion 103.

Specifically, one end of the mounting frame unit 200 is hinged to the shield portion 103, and the mounting frame unit may be rotated in a clockwise or counterclockwise direction with respect to the shield portion 103 with the one end of the mounting frame unit 200 as a rotation center axis.

Referring to FIGS. 4 and 5a to 5C, the cartridge unit 300 is coupled to the mounting frame unit 200 according to an embodiment of the present disclosure, and the coupling structure between the mounting frame unit 200 and the cartridge unit 300 may open and close the opening 101 formed in the helmet unit 100 by the hinge movement of the mounting frame unit 200 with respect to the helmet unit 100, specifically the shield portion 103.

Referring to FIGS. 1, 4, 5C and 5, the mounting frame unit 200 according to an embodiment of the present disclosure is disposed to be attachable to and detachable from the shield portion 103, and the cartridge unit 300 to be described later may be coupled to the mounting frame unit 200.

Referring to FIG. 4, an inside of the mounting frame unit 200 is formed in a hollow shape, and the cartridge unit 300 may be coupled to the inside of the mounting frame unit 200. In the present disclosure, the mounting frame unit 200 may be formed in a rectangular frame shape.

However, the present invention is not limited thereto, and various modifications may be implemented within the technical idea corresponding to the external shape of the cartridge unit 300 that the outer rim and the inner hollow are formed.

Referring to FIGS. 1 and 5a to 5C, one end of the mounting frame unit 200 according to an embodiment of the present disclosure may be hinged to the shield portion 103.

Accordingly, the mounting frame unit 200 may be rotated in a clockwise or counterclockwise direction with a longitudinal axis of the one end of the mounting frame unit 200 connected to the shield portion 103 as a rotational center axis.

As shown in FIG. 5A, when one surface of the mounting frame unit 200 facing the shield portion 103 is in contact with the helmet unit 100, specifically the shield portion 103 as a whole, the opening 101 formed in the helmet unit 100 is closed by the cartridge unit 300 coupled to the mounting frame unit 200.

As shown FIGS. 5B and 5C, when only the one end of the mounting frame unit 200 facing the shield portion 103 is in contact with the helmet unit 100, specifically the shield portion 103, the remaining area except the one end may be spaced apart from the shield portion 103 while rotating in a clockwise direction (based on FIG. 5B) with the one end as a rotational center axis.

Accordingly, the cartridge unit 300 coupled to the mounting frame unit 200 is also spaced apart from the helmet unit 100, specifically the shield portion 103, and the opening 101 formed in the helmet unit 100 may be opened.

In addition, since the opening 101 formed in the helmet unit 100 is opened, the operator may directly recognize the external situation of the helmet unit 100.

Although not illustrated in the drawing, a spring member having an elastic restoring force may be installed at the one end of the mounting frame unit 200 hinged to the helmet unit 100, specifically the shield portion 103, and a hook portion engaged with the shield portion 103 may be formed on a predetermined area among the remaining areas of the mounting frame unit 200 excluding the one end.

The hook portion according to an embodiment of the present disclosure includes a material capable of elastic deformation, and a hook groove portion (not illustrated) fastened with the hook portion may be formed on one surface of the shield portion 103 facing the hook portion formed in the mounting frame unit 200.

Referring to FIG. 5A, in order to cover the opening 101 formed in the helmet unit 100 with the mounting frame unit 200, the operator may rotate the mounting frame unit 200 in a clockwise direction (based on FIG. 5A) with the one end of the mounting frame unit 200 as a rotation center axis to contact the shield portion 103.

When the mounting frame unit 200 is rotated counterclockwise (based on FIG. 5A), the hook portion formed in the mounting frame unit 200 is fastened to the hook groove portion facing the hook portion and formed in the shield portion 103, so that the mounting frame unit 200 may be maintained in contact with the shield portion 103.

Referring to FIGS. 5B and 5C, the spring member (not illustrated) is installed at the one end of the mounting frame unit 200 hinged to the shield portion 103, and the spring member may have an elastic restoring force in the direction where the mounting frame unit 200 is spaced apart from the shield portion 103.

Accordingly, when the operator releases the fastening between the hook portion formed in the mounting frame unit 200 and the hook groove portion formed in the shield portion 103, the spring member pushes the mounting frame unit 200 in a direction away from the shield portion 103, so that the mounting frame unit 200 rotates in a clockwise direction (based on FIG. 5B) with the one end hinged to the shield portion 103 as a rotation center axis.

Referring to FIGS. 1, 2a, 4, 5a and 5, the cartridge unit 300 according to an embodiment of the present disclosure is coupled to the mounting frame unit 200, and it is disposed in a path of light generated during a welding operation to secure the operator's view and to protect the operator' vision.

Referring to FIG. 2A, the cartridge unit 300 according to an embodiment of the present disclosure may include a housing portion 310, a filter portion 320, a panel portion 330, a glass portion 350 and an information display portion 370.

Referring to FIG. 2A, the housing portion 310 of the present disclosure forms an exterior of the cartridge unit 300 and may be coupled to the mounting frame unit 200. Specifically, the housing portion 310 may be coupled to the inside of the mounting frame unit 200.

Referring to FIG. 4, one end of the cartridge unit 300 may be hinged to the mounting frame unit 200.

Accordingly, the cartridge unit 300 may be rotated in a clockwise or counterclockwise direction (based on FIG. 4) with the one end of the cartridge unit 300 hinged to the mounting frame unit 200 as a rotational center axis.

Referring to FIGS. 2A and 4, the housing portion 310 according to an exemplary embodiment of the present disclosure may have a rectangular panel shape. However, it is not limited thereto, and various modifications may be implemented, such as being formed in other polygonal shapes.

An opening region penetrating in the front and rear direction may be formed in the housing portion 310, and a filter portion 320, a panel portion 330, a glass portion 350 and an information display portion 370 may be stacked in the opening region.

An optical sensor portion (reference sign is not given) detecting external light, an electronic control portion controlling the light shielding of the panel portion 330 (reference sign is not given) and a battery portion (reference sign is not given) supplying power to drive the cartridge unit 300 may be installed in the housing portion 310.

Although not illustrated in the drawing, a spring member having an elastic restoring force may be installed at one end of the housing portion 310 hinged to the mounting frame unit 200, and a hook portion engaged with the mounting frame unit 200 may be formed on a predetermined area among the remaining areas of the housing portion 310 excluding the one end.

The hook portion according to an embodiment of the present disclosure includes a material capable of elastic deformation, and a hook groove portion (not illustrated) fastened with the hook portion may be formed on one surface of the mounting frame unit 200 facing the hook portion formed in the housing portion 310.

Referring to FIGS. 4, 5B and 5C, in order to cover the inside of the mounting frame unit 200 with the housing portion 310, the operator may rotate the housing portion 310 in a clockwise direction (based on FIG. 5B) with the one end of the housing portion 310 as a rotational center axis to contact with the mounting frame unit 200.

Referring to FIGS. 4, 5B and 5C, when the housing portion 310 is rotated counterclockwise (based on FIG. 5B), the hook portion formed in the housing portion 310 is fastened to the hook groove portion facing the hook portion and formed in the mounting frame unit 200, so that the cartridge unit 300, specifically the housing portion 310 may be maintained in contact with the mounting frame unit 200.

Referring to FIGS. 5B and 5C, the spring member (not illustrated) is installed at the cartridge unit 300 hinged to the mounting frame unit 200, specifically the one end of the housing portion 310, and the spring member may have an elastic restoring force in a direction where the housing portion 310 is spaced apart from the mounting frame unit 200.

Accordingly, when the operator releases the engagement between the hook portion formed in the housing portion 310 and the hook groove portion formed in the mounting frame unit 200, the spring member pushes the housing portion 310 in a direction away from the mounting frame unit 200, so that the housing portion 310 rotates in a clockwise direction (based on FIG. 5C) with the one end hinged to the mounting frame unit 200 as a rotation center axis.

Referring to FIGS. 5A to 5C, the mounting frame unit 200 is primarily hinged to the helmet unit 100 according to an embodiment of the present disclosure, specifically the shield portion 103, and the cartridge unit 300 is secondarily hinged to the mounting frame unit 200, so that a two-step hinge structure may be formed.

Accordingly, in a state in which one surface of the mounting frame unit 200 is in contact with the shield portion 103, the cartridge unit 300 is disposed at a relatively close distance from the operator, and the mounting frame unit 200 is rotated in a clockwise direction (based on FIG. 5B) from the shield portion 103, and the cartridge unit 300 is rotated in a clockwise direction (based on FIG. 5C) with respect to the mounting frame unit 200, so that the cartridge unit 300 including the information display portion 370 may be spaced away from the operators view by a predetermined distance.

That is, the operator may adjust the distance to the cartridge unit 300 for convenience.

The filter portion 320 according to an embodiment of the present disclosure blocks infrared rays and ultraviolet rays generated in a welding operation, and may be disposed most spaced apart from the operator's face. A dielectric multilayer film may be formed on one surface of the filter portion 320 facing the panel portion 330.

When light is incident from the flame generated during the operator's welding operation, infrared and ultraviolet rays of the light are reflected and blocked by the dielectric multilayer film of the filter portion 320, and only visible light passes through the filter portion 320 and is irradiated to the panel portion 330.

Although not illustrated in the drawing, various modifications such as a protective glass (not illustrated in the drawing) is disposed on the front side of the filter portion 320 (on the left side of FIG. 2A) to prepare for accidents such as sparks that occur during the welding operation are possible.

A coating layer capable of preventing fogging or moisture may be formed on the front surface of the filter portion 320 according to an exemplary embodiment of the present disclosure using a hydrophilic coating material or the like. Accordingly, it is possible to prevent contaminants from adhering to the filter portion 320.

Specifically, the coating layer formed on the front surface of the filter portion 320 may include a hydrophilic photocatalytic material such as titanium dioxide ($TiO_2$) having self-cleaning ability to prevent adsorption of organic materials around the welding operation.

Referring to FIG. 2A, the panel portion 330 according to an exemplary embodiment of the present disclosure is coupled to the filter portion 320 and may be disposed on the operators face side relative to the filter portion 320.

The panel portion 330 may include an LCD panel, and may selectively block visible light generated in the welding operation.

At least one or more of the panel portion 330 may be provided, and transmittance of visible light may be adjusted because the at least one or more panel portions 330a and 330b are disposed.

The panel portion 330 may control light shielding by receiving an electrical signal from the electronic control portion installed in the housing portion 310.

Referring to FIG. 2A, two panel portions 330a and 330b according to an embodiment of the present disclosure are provided, but are not limited thereto, and various modifications such as three or more may be implemented.

Referring to FIG. 2A, the glass portion 350 according to an embodiment of the present disclosure is disposed between the panel portion 330 and the face of the operator, and is directly or indirectly coupled to the panel portion 330 so that the panel portion 330 may be prevented from being damaged by external foreign matter. The glass portion 350 may include a transparent material.

Referring to FIG. 2A, the information display portion 370 to be described later is disposed between the glass portion 350 and the panel portion 330, but is not limited thereto, and various modifications such as the information display portion 370 is arranged between the glass portion 350 and the operator's face may be implemented.

Referring to FIG. 2A, the information display portion 370 according to an embodiment of the present disclosure is coupled to the glass portion 350, and work information related to the welding operation may be visually displayed on it.

In FIG. 2A, the information display portion 370 is disposed on the front side of the glass portion 350 (on the left as in FIG. 2A), but is not limited thereto, and various modifications such as being disposed on the rear side of the glass portion 350 (on the right as in FIG. 2A) may be implemented.

The information display portion 370 according to an embodiment of the present disclosure may include an LCD panel made of a transparent material.

Accordingly, by the information display portion 370, the operator may recognize an external situation through the outside the information display portion 370, the panel portion 330 and the filter portion 320, and may recognize work information displayed on the information display portion 370 at the same time.

In addition, since the work information is displayed on the information display portion 370, the operator may check information related to the operation in real time during the welding operation without taking off the helmet unit 100, thereby improving user convenience.

The information display portion 370 according to an embodiment of the present disclosure may receive power from the battery portion installed in the housing portion 310 to visually display the work information on the information display portion 370.

The information display portion 370 is electrically connected to the electronic control portion and receives an electrical signal to visually display the work information related to the welding operation on the information display portion 370.

Referring to FIG. 2A, the size of the information display portion 370 may be the same as the size of the panel portion 330 or the glass portion 350, but is not limited thereto, and it is possible to implement various modifications such as being formed smaller than the size of the panel portion 330 or the glass portion 350.

Referring to FIGS. 3A to 3j, the horizontal length of the information display portion 370 may be formed equal to that of the panel portion 330 or the glass portion 350, and the vertical length may be formed smaller than that of the panel portion 330 or the glass portion 350.

When the vertical length of the information display portion 370 is formed to be smaller than that of the panel portion 330 or the glass portion 350, the information display portion 370 may be located on the upper or lower side based on the center of the panel portion 330 or the glass portion 350.

In addition, the vertical length of the information display portion 370 may be formed equal to that of the panel portion 330 or the glass portion 350, and the horizontal length of the information display portion may be formed to be smaller than that of the panel portion 330 or the glass portion 350.

When the horizontal length of the information display portion 370 is formed to be smaller than that of the panel portion 330 or the glass portion 350, the information display portion 370 may be located on the left or right side with respect to the center of the panel portion 330 or the glass portion 350.

In addition, both the horizontal length and the vertical length of the information display portion 370 may be formed to be relatively smaller than the horizontal length and vertical length of the panel portion 330 or the glass portion 350, wherein the information display portion 370 may be located on the center of the panel portion 330 or the glass portion 350, and various modifications such as being located on the upper left, upper right, lower left, and lower right based on the center may be implemented.

In other words, when the information display portion 370 is formed to have a relatively smaller area than the panel portion 330 or the glass portion 350, it is located on a central portion of the front or rear surface of the glass portion 350, and various modifications such as being disposed on the left side, the right side, the upper side and the lower side may be implemented.

Referring to FIGS. 1, 5a, 5, and 7, the movement control unit 500 according to an embodiment of the present disclosure is installed in the helmet unit 100, is connected to the mounting frame unit 200, and is possible to control the movement of the mounting frame unit 200 by transmitting power to the mounting frame unit 200.

The movement control unit 500 according to an embodiment of the present disclosure may include a first knob 510 and a second knob 530. The movement control unit 500 may control a first axis movement and a second axis movement of the mounting frame unit 200.

In the present specification, the first axis refers to a moving axis to the front or rear of the mounting frame unit 200 (left and right direction based on FIG. 5), and the second axis is a moving axis to the upper or lower side of the mounting frame unit 200 (vertical direction based on FIG. 5).

Referring to FIGS. 5 and 7, the first knob 510 according to an embodiment of the present disclosure controls the movement of the mounting frame unit 200 to the first axis, and may be rotatably coupled to the helmet unit 100.

The first knob 510 may be formed in a dial knob manner, and may be rotated clockwise or counterclockwise with the center of the first knob 510 as a rotation center axis.

As the first knob 510 is rotated, the mounting frame unit 200 and the cartridge unit 300 coupled to the mounting frame unit 200 may move forward or backward (see FIG. 5).

The first knob 510 may be mechanically connected to the mounting frame unit 200 and may be provided with a gear that converts the rotational motion of the first knob 510 into a linear motion of the mounting frame unit 200.

Due to this, the operator may move the mounting frame unit 200 forward or backward (left and right directions based on FIG. 5) based on the operator's face with a simple operation of gripping the first knob 510 and rotating it in a clockwise or counterclockwise direction.

As the mounting frame unit 200 is moved forward or backward based on the operator's face, the cartridge unit 300 hinged to the mounting frame unit 200 is also moved forward or backward, and the focal length may be adjusted accordingly.

Referring to FIGS. 5 and 7, the second knob 530 according to an embodiment of the present disclosure controls the movement of the mounting frame unit 200 to the second axis orthogonal to the first axis, and it may be rotatably coupled to the helmet unit 100.

Like the first knob 510, the second knob 530 may be formed in a dial knob manner, and may be rotated clockwise or counterclockwise with the center of the second knob 530 as a rotation center axis.

The second knob 530 according to an exemplary embodiment of the present disclosure may be coupled to the first knob 510 while sharing a rotation center axis. The second knob 530 may be formed to have a relatively larger area than the first knob 510 in order to distinguish it from the first knob 510.

However, the present invention is not limited thereto, and various modifications such as that the second knob 530 is formed to have a relatively smaller area than the first knob 510 may be implemented.

Referring to FIG. 5, as the second knob 530 according to an embodiment of the present disclosure is rotated, the mounting frame unit 200 and the cartridge unit 300 coupled to the mounting frame unit 200 may be moved upward or downward (refer to FIG. 5).

The second knob 530 may be mechanically connected to the mounting frame unit 200, and may be provided with a gear that converts the rotational motion of the second knob 530 into a linear motion of the mounting frame unit 200.

Due to this, the operator may move the mounting frame unit 200 upward or downward based on the operators face (left and right directions based on FIG. 5) with a simple operation of gripping the second knob 530 and rotating it clockwise or counterclockwise.

As the mounting frame unit 200 is moved upward or downward based on the operator's face, the cartridge unit 300 hinged to the mounting frame unit 200 is also moved upward or downward, and the heights of the mounting frame unit 200 and the cartridge unit 300 disposed on the front side of the operator may be adjusted.

A wing portion 531 may protrude along an outer peripheral surface of the second knob 530 according to an exemplary embodiment of the present disclosure. At least one wing portion 531 may be provided, and may be disposed at an equal angle with respect to the center of the second knob 530.

As the wing portion 531 protrudes along the outer circumferential surface of the second knob 530, the operator may easily distinguish it from the first knob 510 in which the wing portion 531 is not protruded and may rotate the second knob 530 over the protruding wing portion 531 with a finger, so that the operation convenience is improved.

Figure 2B:
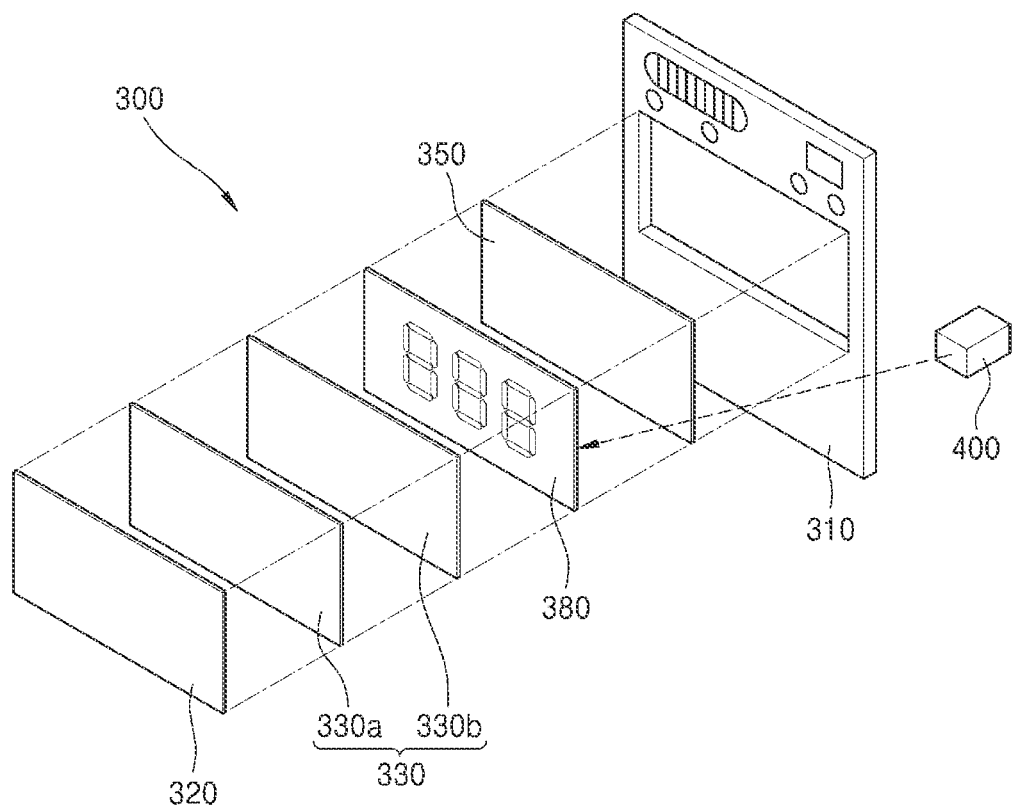
FIG. 2B is an exploded perspective view illustrating a cartridge unit according to another embodiment of the present disclosure.
Figure 3A:
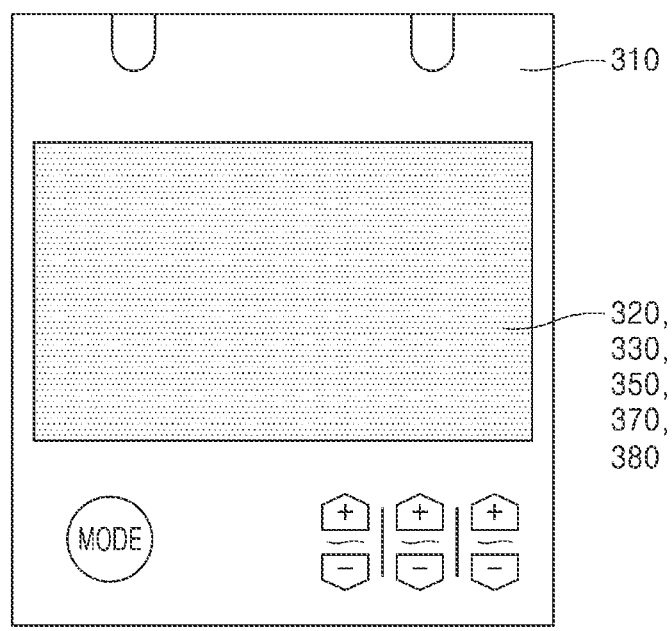
FIGS. 3A to 3J are rear views illustrating the cartridge unit according to embodiments of the present disclosure.
Figure 3B:
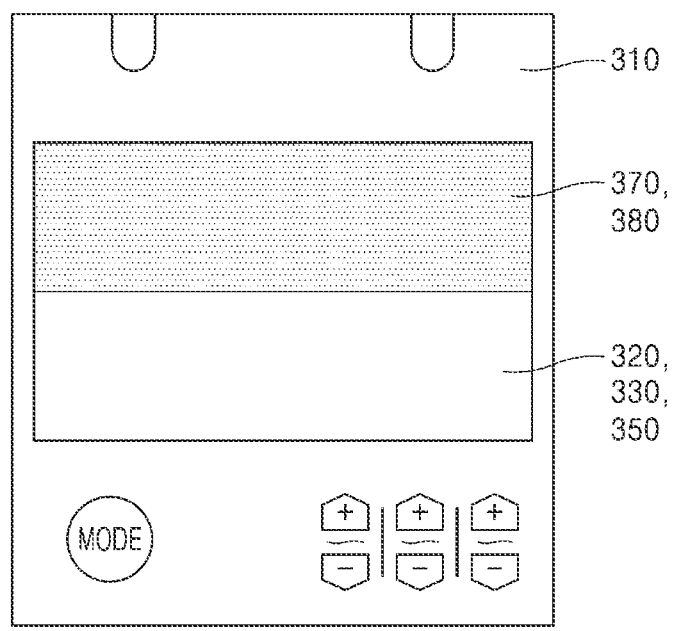
Figure 3C:
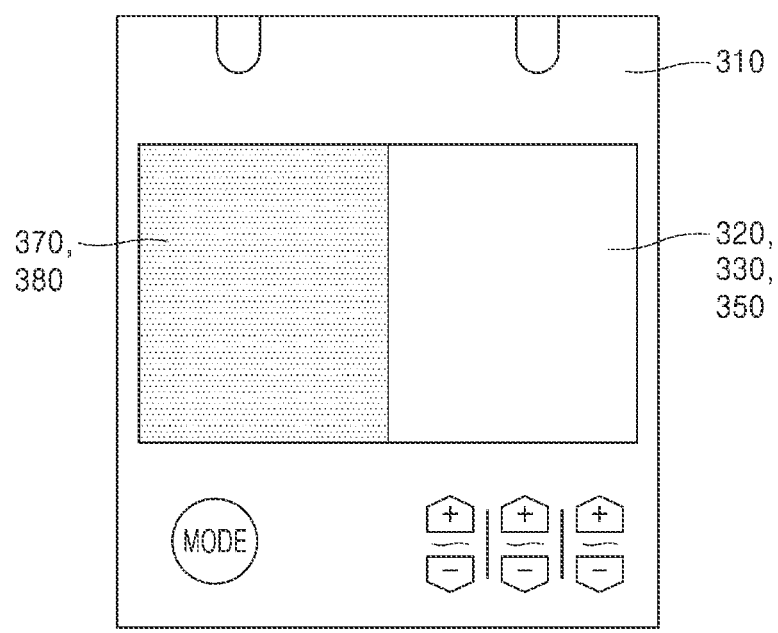
Figure 3D:
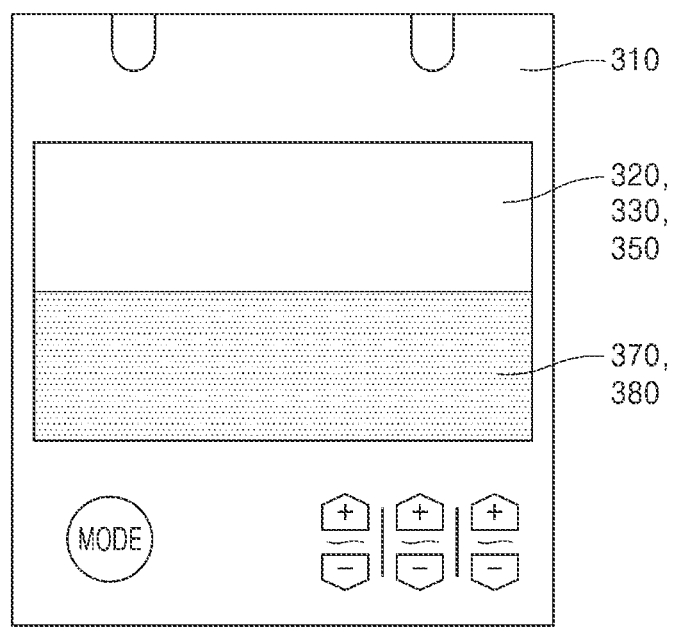
Figure 3E:
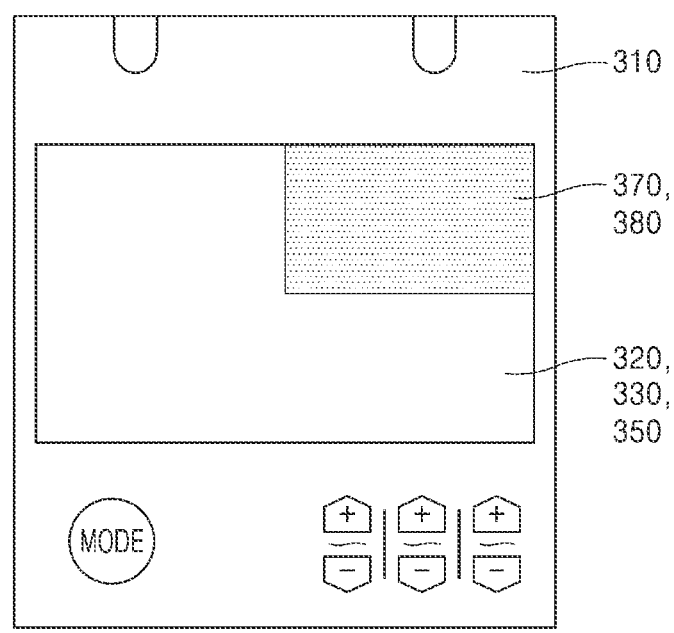
Figure 3F:
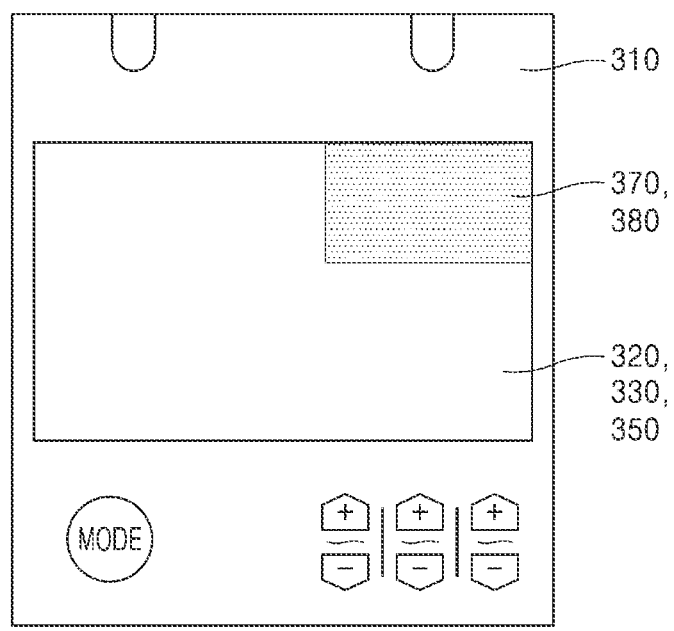
Figure 3G:
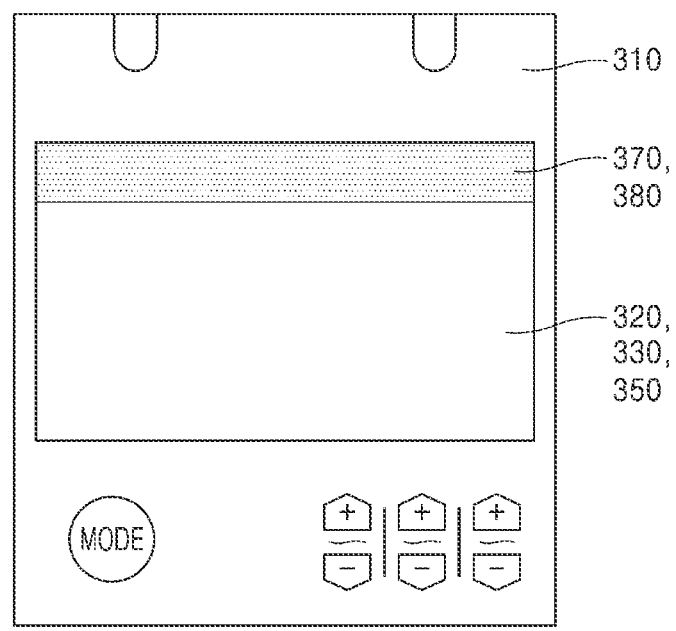
Figure 3H:
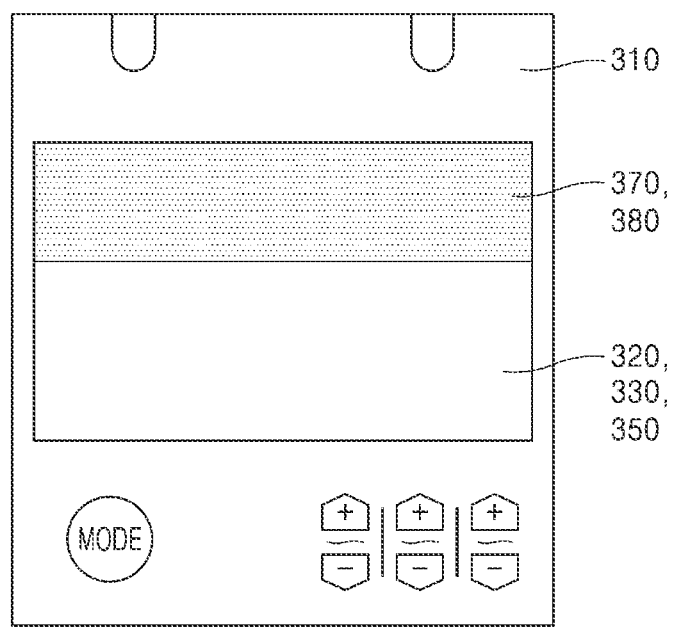
Figure 3I:
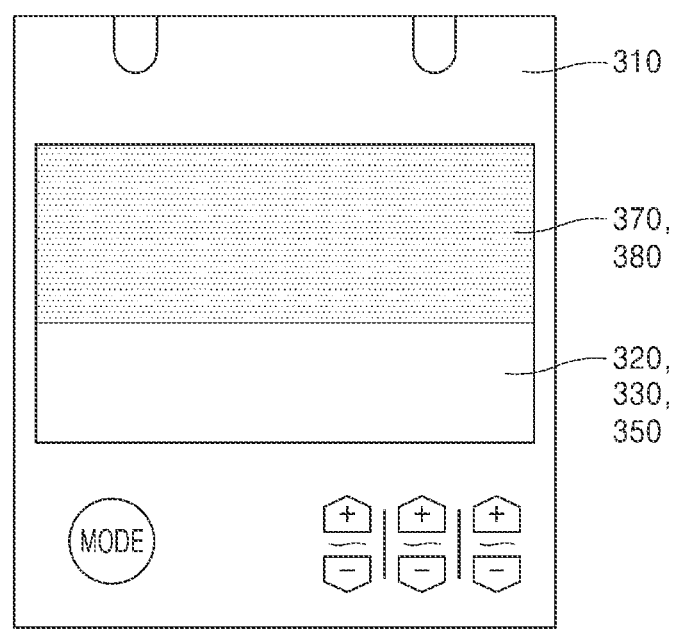
Figure 3J:
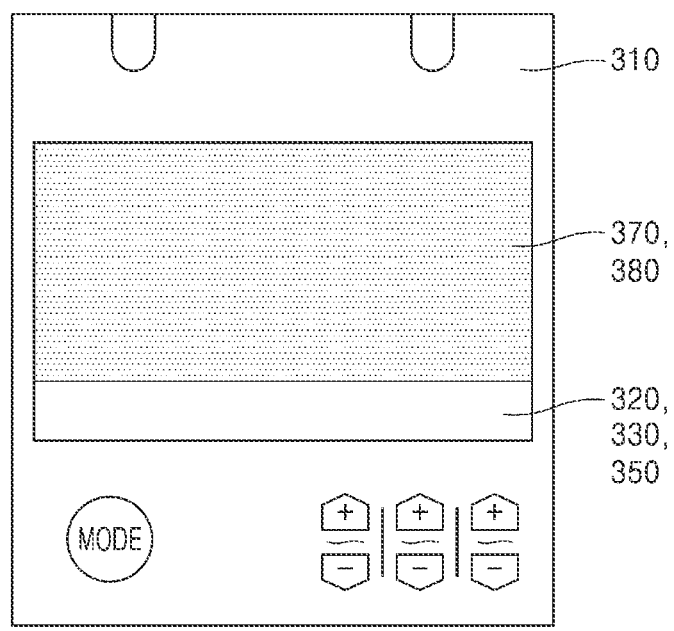

FIG. 2B is an exploded perspective view illustrating a cartridge unit according to another embodiment of the present disclosure. Referring to FIG. 2B, an information display portion 380 according to another embodiment of the present disclosure may include an anti-reflection (AR) coating layer made of a transparent material.

In FIG. 2B, the information display portion 380 is disposed on the front side of the glass portion 350 (left side in FIG. 2B), but is not limited thereto, and various modifications such as being disposed on the rear side of the glass portion 350 (right side in FIG. 2B) are implemented.

Due to the formation of the anti-reflection coating layer on the information display portion 380, the refractive index of visible light passing through the panel portion 330 of the light generated during the welding operation decreases, thereby increasing the light transmittance and minimizing diffuse reflection.

Of course, various modifications such as that the information display portion 380 is disposed on both the front and rear sides of the glass portion 350 may be implemented.

Referring to FIG. 2B, the size of the information display portion 380 may be the same as that of the panel portion 330 or the glass portion 350, but is not limited thereto, and various modifications such as being formed relatively smaller than that of the panel portion 330 or the glass portion 350 may be implemented.

Referring to FIGS. 3A to 3j, the horizontal length of the information display portion 380 may be formed equal to that of the panel portion 330 or the glass portion 350, and the vertical length may be formed smaller than that of the panel portion 330 or the glass portion 350.

When the vertical length of the information display portion 380 is formed smaller than that of the panel portion 330 or the glass portion 350, the information display portion 380 may be located on the upper or lower side based on the center of the panel portion 330 or the glass portion 350.

In addition, the vertical length of the information display portion 380 may be formed equal to that of the panel portion 330 or the glass portion 350, and the horizontal length may be formed to be smaller than that of the panel portion 330 or the glass portion 350.

When the horizontal length of the information display portion 380 is formed to be smaller than that of the panel portion 330 or the glass portion 350, the information display portion 380 may be located on the left or right side with respect to the center of the panel portion 330 or the glass portion 350.

In addition, both the horizontal length and the vertical length of the information display portion 380 may be formed to be relatively smaller than the horizontal length and the vertical length of the panel portion 330 or the glass portion 350, in which case the information display portion 380 may be located on the center of the panel portion 330 or the glass portion 350, and various modifications such as being located on the upper left, upper right, lower left, and lower right based on the center may be implemented.

In other words, when the information display portion 380 is formed to have a relatively smaller area than the panel portion 330 or the glass portion 350, it is located on a central portion of the front or rear surface of the glass portion 350, and various modifications such as being disposed on the left side, the right side, the upper side and the lower side may be implemented.

Referring to FIG. 2B, an irradiation unit 400 according to another embodiment of the present disclosure is installed inside the helmet unit 100 and may be specifically positioned on the inner surface of the helmet unit 100. The irradiation unit 400 may irradiate a light source toward the information display portion 380 formed in a predetermined thickness.

Since the light source is irradiated from the irradiation unit 400 toward the information display portion 380, the work information related to the welding operation may be visually displayed on the information display portion 380.

Referring to FIG. 2B, the light source irradiated from the irradiation unit 400 according to another embodiment of the present disclosure is irradiated to form a predetermined angle with one surface of the information display portion 380, and the predetermined angle in the present disclosure is 45 degrees, but not limited to this, it is possible to implement various modifications within the technical idea that an image may be formed on the information display portion 380 by the light source irradiated from the irradiation unit 400.

The irradiation unit 400 according to another embodiment of the present disclosure may receive power from a battery portion installed in a housing portion 310 and irradiate a light source toward the information display portion 380. The irradiation unit 400 may be electrically connected to an electronic control portion, may receive an electrical signal, and may visually display the work information related to the welding operation on the information display portion 380 formed of the anti-reflection coating layer.

Referring to FIG. 2B, unlike the information display portion 370 according to an embodiment of the present disclosure, the information display portion 380 according to another embodiment of the present disclosure includes the anti-reflection coating layer made of the transparent material instead of the LCD panel made of the transparent material, and accommodates the light source irradiated from the irradiation unit 400 so that work information related to the welding operation is visually displayed on the information display portion 380. Meanwhile, since there is no difference between the information display units 370 and 380 in the configuration of the helmet unit 100, mounting frame unit 200, the housing portion 310, filter portion 320, the panel portion 330, the glass portion 350 and the movement control unit 500, detailed descriptions thereof will be omitted.

In the welding protector according to the embodiments of the present disclosure, the information display portion formed of the transparent material is disposed on the front or rear side of the glass portion, and information related to the welding operation is visually displayed, so that the operator may check the work information related to the welding operation directly and immediately without taking off the helmet unit, thereby improving user convenience.

Since the information display portion according to another embodiment of the present disclosure includes the anti-reflection coating layer made of the transparent material, the refractive index of visible light may be lowered to improve transmittance, and the diffuse reflection of visible light passing through the panel portion may be minimized, so that a clear view may be secured during the welding operation.

The information display portion according to the exemplary embodiments of the present disclosure may be formed in various sizes, and may be bonded to various positions at the front or rear side of the glass portion, thereby improving user convenience.

The specific implementations described in the present disclosure are exemplary, and do not limit the scope of the present disclosure in any way. In addition, the connection or connection members of lines between the components illustrated in the drawings are exemplarily illustrated as functional connections and/or physical or circuit connections, and may be represented as various functional connections, physical connections, or circuit connections that may be replaced in an actual apparatus. In addition, if there is no specific description such as "essential" or "important", the components may not be necessarily required for application of the present invention.

Therefore, the spirit of the present invention is not limited to the above-described embodiments, and it will be understood that not only the claims described below but also all ranges equally or equivalently changed from the claims fall within the scope of the present invention.

The invention claimed is:

1. A welding protector for protecting an operator, the welding protector comprising:
   a helmet unit having an opening and a shield portion surrounding the opening;
   a mounting frame unit including a first end and a second end, wherein the mounting frame unit is hingeably coupled to the shield portion at the first end;
   a movement control unit installed on the helmet unit, connected to the mounting frame unit, and controlling movement of the mounting frame unit by transmitting power to the mounting frame unit; and
   a cartridge unit hingeably coupled to the mounting frame unit adjacent the second end and disposed on a path of light generated during a welding operation,
   wherein the cartridge unit includes:
      a filter portion;
      a panel portion coupled to the filter portion and configured to be disposed closer to a face side of the operator than the filter portion;
      a glass portion configured to be disposed closer to the face side of the operator than the panel portion; and
      an information display portion combined with the glass portion and visually displaying work information,
   wherein the movement control unit includes:
      a first knob formed as a dial, wherein the first knob is configured to be rotated clockwise or counterclockwise about a rotation center axis located at a center of the first knob, and to move the mounting frame unit and the cartridge unit coupled to the mounting frame unit along a first linear axis in response to rotation of the first knob; and
      a second knob formed as a dial, wherein the second knob is configured to be rotated clockwise or counterclockwise about the rotation center axis that is located at a center of the second knob, and to move the mounting frame unit and the cartridge unit coupled to the mounting frame unit along a second linear axis orthogonal to the first axis in response to rotation of the second knob, wherein:
         the second knob is operably coupled to the first knob while sharing the rotation center axis, and has a larger area than the first knob in order to distinguish the second from the first knob and
         the second knob further includes at least one wing portion configured to protrude along an outer peripheral surface of the second knob.

2. The welding protector of claim 1, further comprising an irradiation unit installed inside the helmet unit and irradiating a light source to the information display portion, wherein the information display portion includes an anti-reflection (AR) coating layer made of a transparent material.

3. The welding protector of claim 1, wherein the mounting frame unit is attachable and detachable from the shield portion.

* * * * *